US010018379B2

(12) United States Patent
Shenhav

(10) Patent No.: US 10,018,379 B2
(45) Date of Patent: Jul. 10, 2018

(54) ELECTROMAGNETIC RADIATION SPREADING FOR DIRECT INDOOR USES

(71) Applicant: Yaron Shenhav, Herzliya (IL)

(72) Inventor: Yaron Shenhav, Herzliya (IL)

(73) Assignee: Sol Cold Ltd., Herzlia (IL)

( * ) Notice: Subject to any disclaimer, the term of this patent is extended or adjusted under 35 U.S.C. 154(b) by 19 days.

(21) Appl. No.: 14/588,992

(22) Filed: Jan. 5, 2015

(65) Prior Publication Data
US 2015/0260431 A1 Sep. 17, 2015

Related U.S. Application Data

(60) Provisional application No. 61/923,781, filed on Jan. 6, 2014.

(51) Int. Cl.
A61N 5/06 (2006.01)
F24J 2/38 (2014.01)
G02B 19/00 (2006.01)
G02B 27/10 (2006.01)
H01L 31/054 (2014.01)
F24J 2/06 (2006.01)
F21S 11/00 (2006.01)
F24J 2/08 (2006.01)

(52) U.S. Cl.
CPC .............. *F24J 2/38* (2013.01); *A61N 5/0616* (2013.01); *F24J 2/06* (2013.01); *G02B 19/0042* (2013.01); *G02B 27/1006* (2013.01); *H01L 31/0549* (2014.12); *A61N 2005/063* (2013.01); *A61N 2005/0657* (2013.01); *A61N 2005/0661* (2013.01); *A61N 2005/0665* (2013.01); *F21S 11/005* (2013.01); *F21S 11/007* (2013.01); *F24J 2/062* (2013.01); *F24J 2/067* (2013.01); *F24J 2/08* (2013.01); *Y02E 10/44* (2013.01); *Y02E 10/47* (2013.01); *Y02E 10/52* (2013.01)

(58) Field of Classification Search
CPC ........................ G02B 19/0042; G02B 27/1006
USPC ................ 320/101; 250/493.1; 359/591–598
See application file for complete search history.

(56) References Cited

U.S. PATENT DOCUMENTS

| 4,389,085 A * | 6/1983 | Mori ........................ F21S 11/00 359/591 |
| 4,411,490 A * | 10/1983 | Daniel ..................... F21S 11/00 126/648 |
| 2012/0073569 A1* | 3/2012 | Hassan ................... D06F 58/02 126/698 |
| 2014/0055844 A1* | 2/2014 | Cormier ............ H01S 3/094053 359/341.3 |
| 2014/0126062 A1* | 5/2014 | Heo .................... G02B 19/0042 359/591 |
| 2014/0251411 A1* | 9/2014 | Ganti ..................... H01L 31/18 136/246 |

* cited by examiner

Primary Examiner — Kristen Matter
(74) Attorney, Agent, or Firm — IPAttitude Ltd.; S. Yarus

(57) ABSTRACT

A system and method for converting the sun's electromagnetic radiation to work, where the system collects the radiation with at least first one lens or mirror. Splitting means split the radiation spectrum, preferably using prism, set of prisms, diffraction grating, or set of beam splitters. Second one lens or mirror is configured to collect the radiation separately for each wavelength range. At least one fiber optic cable is configured to transfer the radiation to electromagnetically or electrically operated appliance, device or machine.

15 Claims, 9 Drawing Sheets

ELECTROMAGNETIC RADIATION SPREADING FOR DIRECT INDOOR USES

TECHNICAL FIELD

The present invention pertains to direct conversion of electromagnetic radiation to work. Particularly, the present invention pertains to system and method for collecting solar radiation, dividing and streaming it to radiation ranges as input power to appliances and equipment and/or to electricity operated appliances and equipment.

BACKGROUND

Current technology based on solar energy offers different solutions for converting solar energy to electrical or other applicable energy.

US 2009/0250098 describes an array of photovoltaic cells collecting the solar radiation that is split to different ranges of the spectrum. The selective radiation is done possible through use of different materials in the cells in such way that each material has a different energy absorption level. The cells are arranged one on top of the other in such way to achieve maximum absorption in each cell.

US 2009/0250099 describes a similar arrangement of cells as in US 2009/0250098 designed to convert solar energy into heat, and from heat to electricity by dedicated modules.

US 2007/0023079 describes a surface splitting the radiation divided into areas. Each area collects electromagnetic radiation in different angles.

YU 81001 describes a system of lenses, which concentrate the sun energy and a prism which spreads the spectrum evenly. The spectrum is then being collected by photovoltaic cells to generate electricity.

WO 2013/150453 describes a system that splits the electromagnetic radiation into different wavelengths. The device has several areas; each area breaks the radiation and concentrates a specific wavelength.

GB 2456660 describes a system that spreads the sun electromagnetic radiation into separated wavelengths by mirrors and prism. The different wavelengths are then being collected by several p-n semi-conductors adjusted to the spectrum length.

US 2013/214139 describes a system that collects solar electromagnetic radiation into fiber cable and then splits the radiation into heat, white light, and electricity by putting filters along the ray path.

The disadvantages of the solutions detailed above are in the fact that energy converted to electricity loses the majority amount of the total energy. Furthermore, the end product using the electricity loses a great amount of energy as well.

In addition, the solutions detailed above are focused on converting solar energy into electricity. However, a direct use of this energy in the end product can eliminate the energy exchange and thus exploit a far greater percentage of the solar energy.

It is, therefore, an object of the present invention to provide a system that overcomes the disadvantages of the current technology and propose a device that allows direct sunlight in end appliances.

Still another object of the present invention is to provide flexibility in the types of functionalities that can be used simultaneously with the solar energy. As the use of the energy is direct and non-conservative, it is important to have the flexibility to choose the types of uses which operate with this energy depending on actual needs (heating, cooling, filtering, lighting, etc).

Still another object of the present invention is to provide a standard system that provides selected ranges of solar spectrum that can be used as the source of power for any device designed to exploit it. By this the system enables adding new ways to further maximize use of the solar energy.

This and other objects of the present invention will become apparent as the description proceeds.

SUMMARY OF THE INVENTION

The general concept of the system comprises solar spectrum radiation as input, and multiple ranges of radiation as output. Another way to look at it is to take the solar radiation in the frequency/wavelength axis and divide the axis to a plurality of intervals so each output range begins at one point and end at the following one. Each output range is the input power for different appliances producing different outputs mainly: Cooling, Heating and Lighting.

To perform this, the system first collects the solar radiation by a lens/mirror, or a set of lenses/mirrors, spreads the radiation in means such as (but not limiting): a prism, a set of prisms, a diffraction grating or a set of beam splitters, and collects it by a set of lenses/mirrors to match the number of ranges the system sets as output. In one particular embodiment, the lenses and mirrors are made of different materials matching different wavelengths. The sizes of the lenses/mirrors and their location on a grid defines the range which will be collected by each one of them. The radiation shall then be transferred by a fiber optic cable (of any material suitable for transferring the solar range) to its end-product destination, or in some cases, the fiber optic cable itself is the final end-product.

In one particular embodiment, the lenses and the prisms suggested in the proposed diagram can be of glass material but are not limited in material, and can be of any material that allows the transfer of solar radiation. Particular non-limiting examples are transparent polymeric materials such as polystyrene, low density polyethylene, polypropylene and polycarbonate.

In still another embodiment, the mirrors of the present invention are parabolic mirrors off/on axis aiming at concentrating the solar radiation/ranges to the next functionality of the system, e.g. prism/diffraction grating/beam splitters/fiber optic cables.

In one aspect, the present invention provides multiple ranges of spectrum which may be configured and modified according to the needs of the end products so that end products can be developed with the liberty of any range of spectrum as energy input.

In one embodiment, the present invention provides a mechanism to collect electromagnetic radiation from a wide range of sources (as the sun's radiation) and splits the radiation into a plurality of ranges of spectrum. Each range differs from its neighbor ones by breadth of spectrum and position, e.g. range #1 is 380 nm-780 nm, range #2 is 950 nm-1015 nm etc.

In still another embodiment of the invention, each range of electromagnetic radiation is inserted into fiber optic cable that carries it from the system position to the end-product location. In one particular embodiment, the fiber optic can be of any size and material to support the carrying of the radiation.

In another embodiment, a set of lenses/mirrors is implemented in the system to minimize the etendue angle of the optical system.

The fiber optic cable can also be the end-product itself, for example laser cooling of Ytterbium fiber cable will use the fiber optic cable as the means for cooling itself. Accordingly, the invention provides the liberty of using the spectrum range for practically any electromagnetic radiation motivated, e.g. solar radiation, implementation.

The uses of the output of the system can vary. Non-limiting examples are detailed below:

1. Heating, by projecting IR spectrum on black body (or other spectrum absorbing material) to be implemented to heat water, air, oil, or any other material. The heating element is not restricted to IR radiation, and can be used in any part of the solar spectrum.

2. Cooling, by Laser cooling technology, to be implemented to cooling water, air or any other material either by using the fiber optic as the working material or projecting on a working material. The Laser cooling technology uses incoherent/coherent monochromatic spectrum. This can be achieved in using the system by taking a very small wavelength range of the spectrum and creating a semi-laser.

3. Lighting, by taking the visible part of the spectrum and projecting it to light the indoors or other closed or open spaces.

4. Production of Vitamin D, by projecting short spectrum UV radiation (270 nm-300 nm) indoors to allow the creation of vitamin D in the body. The spectrum can be limited further towards the maximum wavelength to create vitamin D (e.g., 295 nm-297 nm).

5. Filtering, by using the UV spectrum, to be implemented to filter water, air, or other materials by projecting the UV spectrum on them.

6. Electricity, manufactured by projecting parts of the spectrum onto photo voltaic cells.

7. Electricity, manufactured by using a Heating element, (1) as illustrated in FIG. 1 to generate electricity with means known today.

Any use of parts of the spectrum can be thought about and implemented using the system. The invention does not limit itself to the uses listed above. Furthermore, any output range of the spectrum can be further filtered for specific wavelengths ranges (within the range) if the end-product requires this.

As the system is aimed at direct use of the spectrum ranges indoors, its installation needs to be in close proximity to a closed structure. In one embodiment, possible installation of the system is on the roof of the structure or outside the walls, or even outside the structure with close proximity to it. In one particular example, the system is installed on the roof of the structure, while the fiber optic cables traveling from the system indoors and connecting to the end-product devices.

In still another particular embodiment, a mechanism for detecting and following the sun is implemented in the system to allow maximum angle and maximum energy input. The mechanism can be of any kind, e.g., GPS, solar amplitude, prerecorded points, mechanical circle, etc.

A further aspect of the installation is the unit installation. A unit may include several described systems connected with each other, moving together while following the sun's position in the sky. That said, the invention is not limited to a particular structure of a unit. Such unit may be configured to include four systems (2×2) or any other array structure suitable for tracking a source of electromagnetic radiation and collecting that radiation.

In view of the above, the present invention provides a system for converting electromagnetic radiation to work, where the system comprises:

at least first one lens or mirror, where at least the first one lens or mirror is configured to collect the electromagnetic radiation;

a prism, a set of prisms, a diffraction grating, a set of beam splitters or any other means to split the solar radiation configured to spread the electromagnetic radiation to wavelength ranges;

at least a second one lens or mirror configured to collect the electromagnetic radiation separately for each one of the wavelength ranges, where the number of the at least second one lens or mirror matches the number of the wavelength ranges;

at least one fiber optic cable configured to transfer the electromagnetic radiation from the at least second lens or mirror to at least one electromagnetically or electrically operated appliance, device or machine; and at least one electromagnetically or electrically operated appliance, device or machine, wherein either the size and location on a grid of the at least second lens or mirror defines each one of the wavelength ranges or the beam splitters define the range projected on the at least second lens or mirror which will be collected by each one of the at least second lens or mirror.

In one particular embodiment, the at least first one lens is made of glass.

In still another embodiment, the at least first one lens is made of at least one transparent polymeric material, where the transparent polymeric material may be selected from polystyrene, low density polyethylene, polypropylene and polycarbonate.

In one particular embodiment, the at least first or second one lens or mirror is parabolic on/off axis and configured to concentrate the electromagnetic radiation or the electromagnetic wavelength ranges.

In still another particular embodiment, the system comprises a plurality of second lenses or mirrors, where the second lenses or mirrors are configured to cover a plurality of elected electromagnetic radiation wavelength ranges of a solar spectrum and configured according to needs of the appliance, device or machine. Any one of the appliance, device or machine is configured to operate with one or more of the elected electromagnetic radiation wavelength ranges of the solar spectrum as energy input.

In still another particular embodiment, the fiber optic cable is configured to be of any size and material to support the transferring of the electromagnetic radiation.

In particular, the fiber optic cable is made of or coated with a laser cooling active material. Laser cooling active materials may be selected from Ytterbium, Yb3+, (with a range of photon emission of 920 nm-1050 nm) or semiconductors of elements of the III-V group such as gallium arsenide quantum wells and cadmium sulphide, the latter having photon emission range of 490 nm-560 nm, Cesium with wavelength of 760 nm-890 nm, 9Be+ with wavelength of around 300 nm and other suitable materials to be found in further research. Other materials suitable for the fiber optic cable or its coating may be selected from semiconductors of the II-VI group. In one particular example, the cable is configured to cool itself.

Still in another particular embodiment, the fiber optic cable is the appliance, device or machine. In particular, the fiber optic cable is a laser cooling of Ytterbium or gallium arsenide or cadmium sulphide or Cesium or 9Be+ fiber cable configured to cool itself.

In one particular embodiment, the system is configured for installation in close proximity to a closed structure. In one particular non-limiting example, the system is located on a roof or outside walls of the closed structure, or outside in close proximity to the closed structure, where the fiber optic cable is connected to the system and travels indoors of the closed structure and connected to the appliance, device or machine.

A source of the electromagnetic radiation may be the sun, where the system further comprises a mechanism for detecting and following the sun. Such mechanism is configured to allow maximum angle and maximum solar energy input. Particularly, the mechanism may be selected from single axis tracking systems or two axis tracking systems. The tracking systems may be sensor-enabled detection or non-sensory enabled detection. Particular non-limiting examples of sensor-enabled detection systems may be solar amplitude sensors and solar position detection sensors. Particular non-limiting examples of non-sensory detection systems may be selected from prerecorded solar location relative to longitude and latitude, GPS tracking system and "dumb" east-west mechanism In one aspect, the present invention also provides a unit installation comprising a plurality of systems, where the plurality of systems is configured to move synchronically with each other and follow movement of a source of electromagnetic radiation. The plurality of systems is configured in array structure suitable for tracking movement of a source of electromagnetic radiation. The unit installation may be configured to include four systems in rectangular array formation.

Further, the source of electromagnetic radiation may be the sun, and the plurality of systems is configured to synchronically follow the position of the sun in the sky.

In one aspect, the present invention provides a method for converting electromagnetic radiation to work, where the method comprises:

collecting electromagnetic radiation from a wide range of electromagnetic radiation emitting sources;

transferring the electromagnetic radiation to a plurality of lenses and/or mirrors;

splitting the electromagnetic radiation to a plurality of electromagnetic radiation wavelength ranges;

transferring the electromagnetic radiation of each one of the wavelength ranges to electromagnetically or electrically operated appliance, device or machine, where the appliance, device or machine is configured to directly receive particular one or more of the plurality of electromagnetic wavelength ranges and operate based on the particular wavelength range(s).

In one particular embodiment, the method of the present invention comprises at least one of:

heating, by projecting IR spectrum on black body;

Cooling with Laser cooling technology, where the cooling is implemented on any responsive material to the laser cooling technology (gas or solid) with the right range of spectrum as stimulator. The material will use to cooling water, air or any other material;

lighting with a visible wavelength range of electromagnetic radiation spectrum and projecting light generated to indoors or other closed or open spaces;

producing Vitamin D, by projecting short spectrum UV radiation (270 nm-300 nm) indoors to allow the creation of vitamin D in a body of a living person;

filtering by projecting UV wavelength range of electromagnetic radiation spectrum to filter water, air or other materials;

producing electricity manufactured by projecting parts of electromagnetic radiation spectrum onto photovoltaic cells;

producing electricity manufactured with a heating element; or directing the electromagnetic radiation for medicinal usages, using specific ranges for medical uses such as: 415 nm used for treating acne, and 280 nm-320 nm for treating Psoriasis, Vitiligo, and skin infection. Exposure to UAV light while the skin is hyper-photosensitive is an effective treatment.

In particular, the Laser cooling technology may use incoherent/coherent semi monochromatic spectrum.

In another embodiment, the spectrum of UV radiation is further limited to maximum wavelength for creating vitamin D (295 nm-297 nm).

The following relates to the accompanying Figures without departing from the spirit of the invention as detailed above.

DETAILED DESCRIPTION OF THE DRAWINGS

Figure 1:
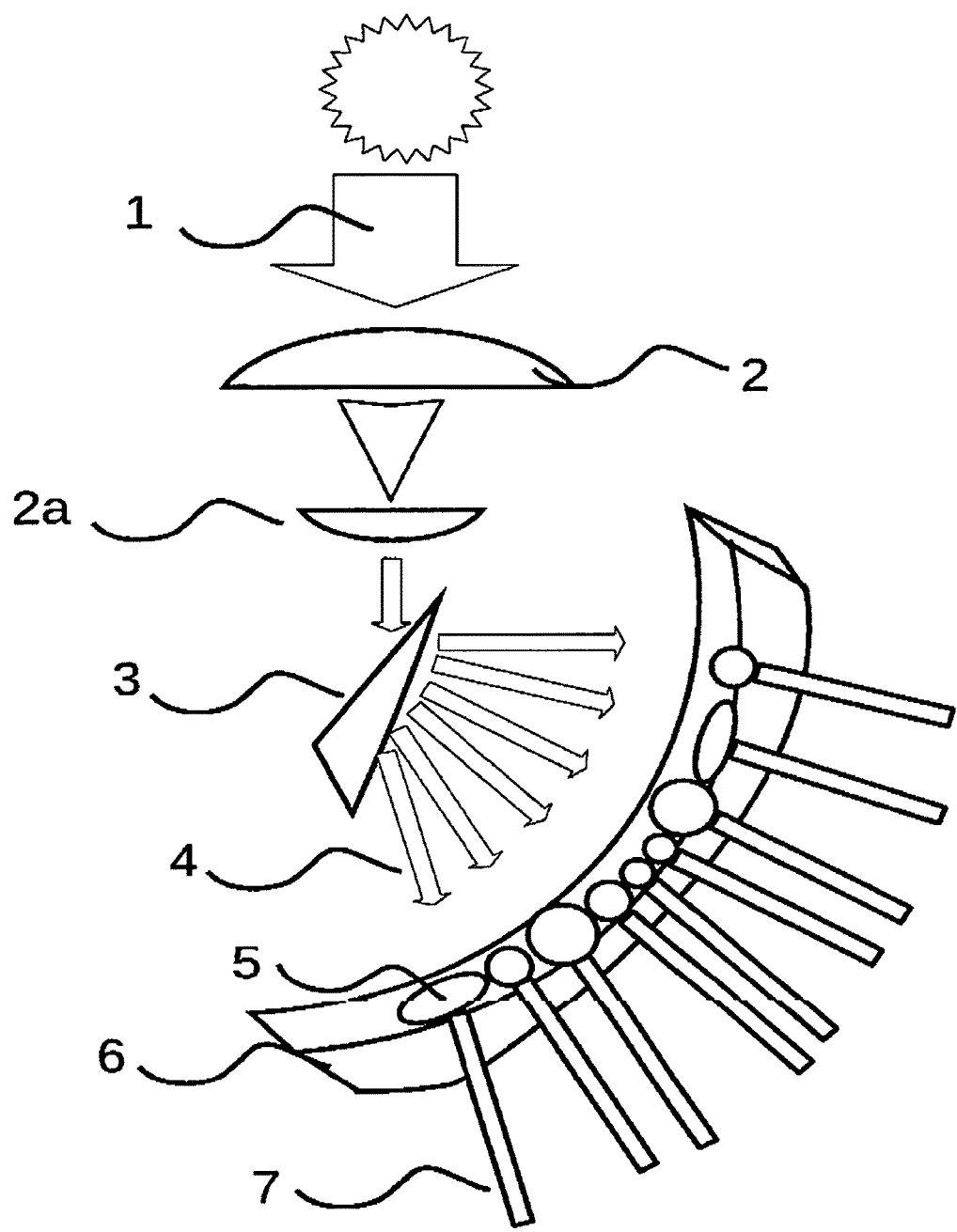
FIG. 1 illustrates the system with its internal components, and is intended to give the look and feel of the proposed system.

Referring to FIG. 1, this Figure illustrates the system of the present invention—the sun solar radiation (1) is received by the set of concentrating lenses/mirrors (2), (2a). The concentrated radiation hits the radiation splitter that can be a prism, a diffraction grating or a set of beam splitters (3) that spreads the radiation (4) either from the shortest wavelength to the longest as with a prism/diffraction grating or directly separated to ranges as with the beam splitters (3).

The spread radiation arrives at the surface (6) and there according to the arrangement of the lenses/mirrors (5)—different ranges of spectrums are collected and inserted into the fiber optic cables (7) to carry each range to its end product destination.

Figure 2:
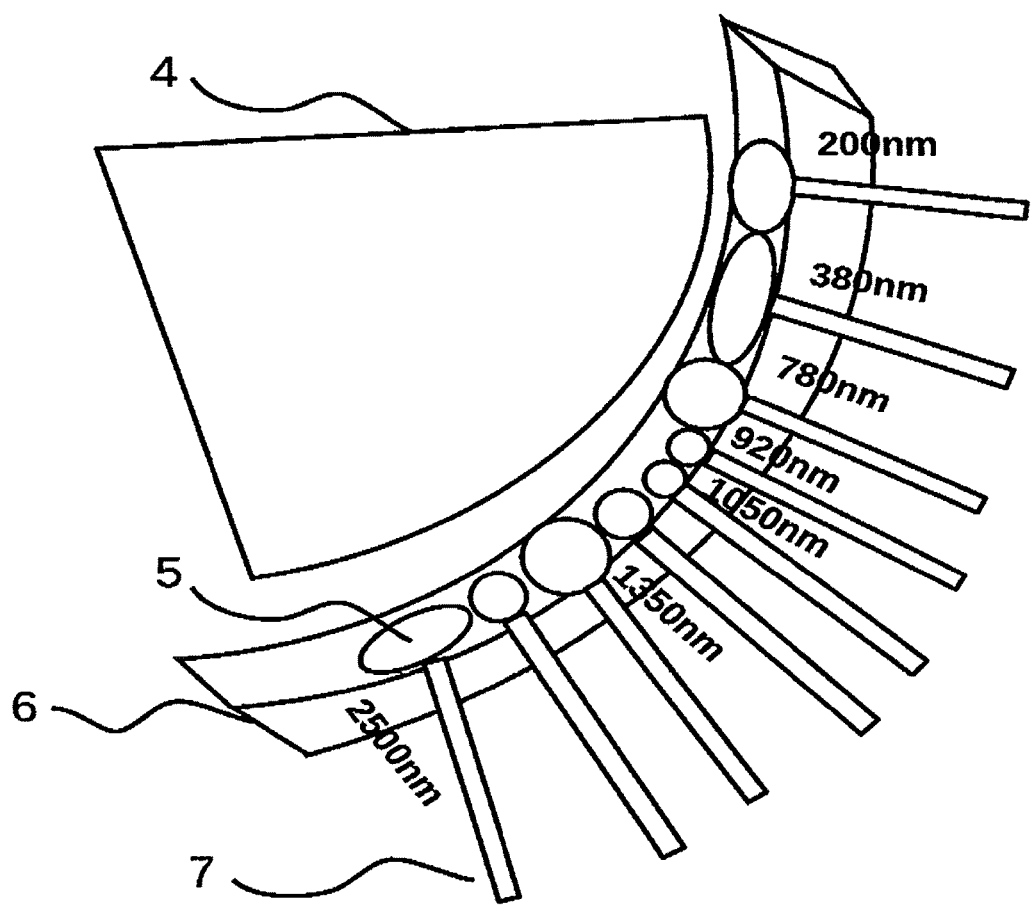
FIG. 2 illustrates the surface subcomponent of the system of the present invention, which is responsible for collecting the selective spectrum ranges, i.e., collecting multiple ranges of the spectrum.

Referring to FIG. 2, this Figure illustrates the surface (6) part of the present invention with its lenses/mirrors (5) and fiber optic cables (7). In the Figure the spread solar spectrum (4) arrives at the surface (6) equipped with nine lenses/mirrors (5) to demonstrate the dividing to multiple ranges of spectrum. On the surface (6) we have marked a ruler of wavelength to assist in determining the correct position of the lenses/mirrors (5). A greater number of ranges can be easily achieved by adding more beam splitters and/or more lenses/mirrors suitable to transfer selected electromagnetic radiation wavelength ranges.

Figure 3:
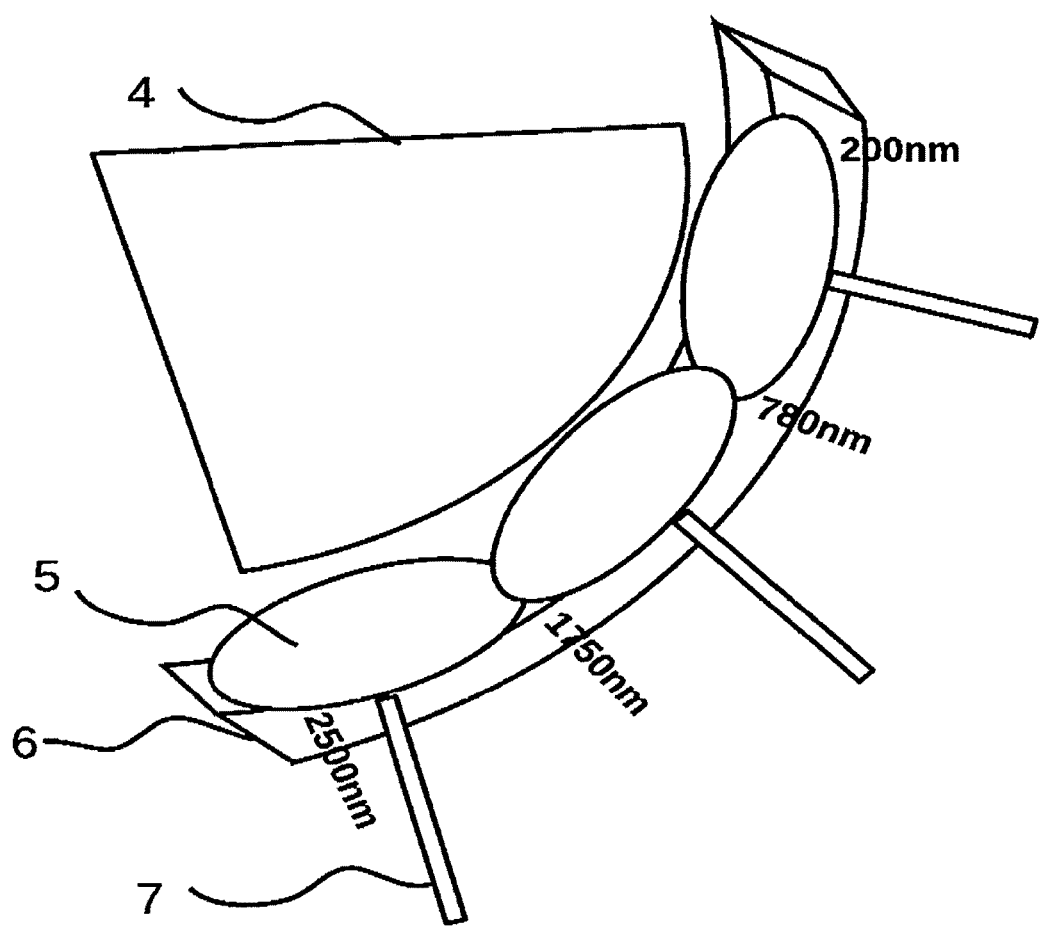
FIG. 3 illustrates the surface subcomponent of the system of the present invention, collecting secluded ranges of the spectrum.

Referring to FIG. 3, this Figure illustrates the surface (6) part of the present invention with its lenses/mirrors (5) and fiber optic cables (7). In the Figure the spread solar spectrum (4) arrives at the surface (6) equipped with three lenses/mirrors (5) to demonstrate the dividing to separate ranges of spectrum. On the surface (6) we have marked a ruler of wavelength to assist in determining the correct position of the lenses/mirrors (5). A smaller number of ranges can be easily achieved by removing more lenses/mirrors until the limit of taking the entire spectrum with a single lens/mirror, or with as minimum of a single beam splitter aiming at a single lens/mirror.

Figure 4:
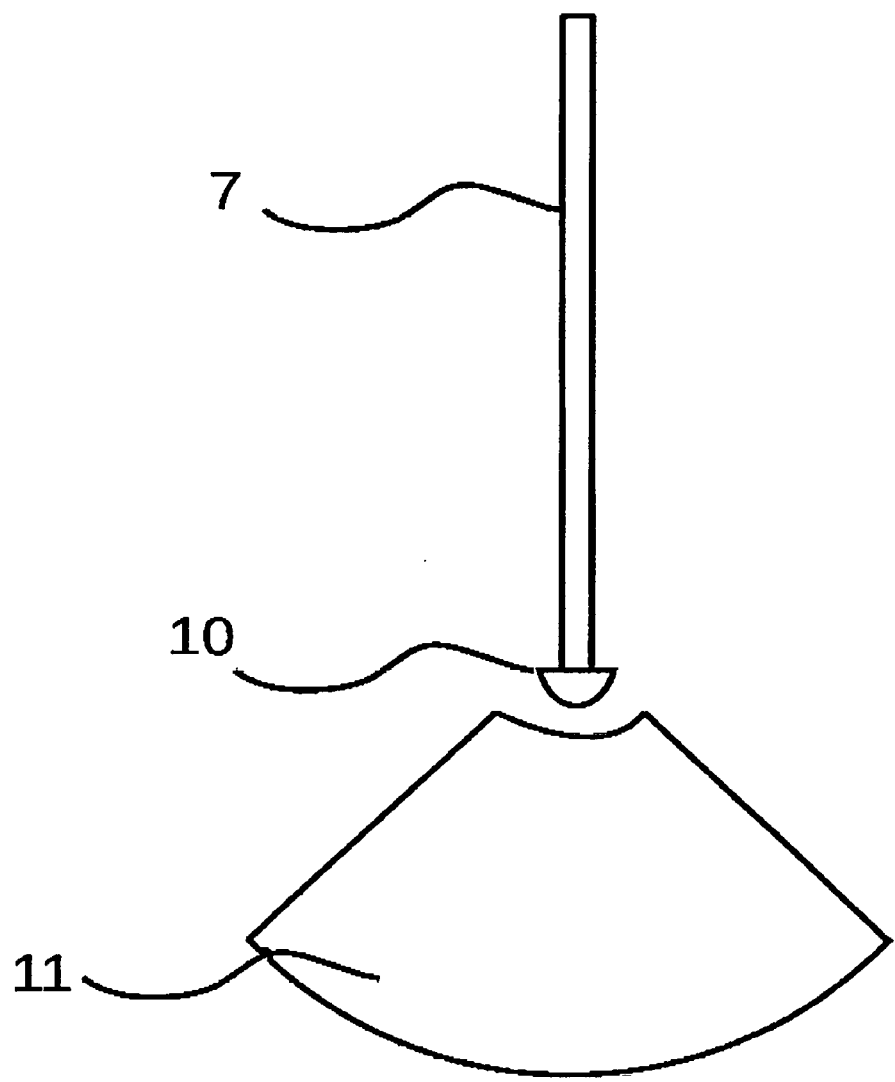
FIG. 4 illustrates an optional use of one range of the spectrum, 380 nm-780 nm as visible light to illuminate the indoors. The same manner can be issued to project the range of 270 nm-300 nm in order to produce Vitamin D.

Referring to FIG. 4, this Figure illustrates an optional use of solar radiation range between 380 nm—780 nm (Visible light). In the example, a spreading lens (10) is connected to the fiber optic cable (7) to spread the visible light (11) carried by the cable. In this example the fiber optic cable (7) already carries the right range of spectrum (380 nm-780 nm) from the system (20) illustrated in FIG. 8, so there is no need for additional filtering. The lens (10) is a spreading lens intended to spread the light in a large volume. This example can be installed in a hole in the ceiling to light the indoors of a building. The same example can also be used to project 270 nm-300 nm with the purpose of generating natural vitamin D indoors.

Figure 5:
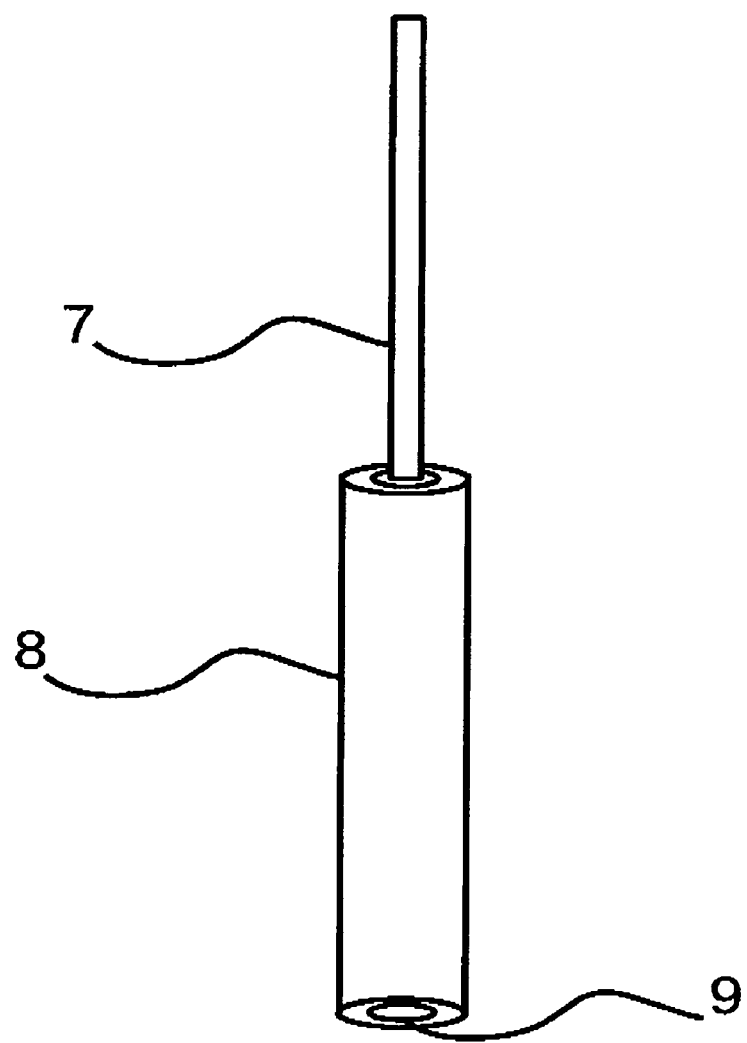
FIG. 5 illustrates another optional use of a different range of the spectrum 920 nm-1050 nm as a method to cool the indoors with Laser Cooling technology.

Referring to FIG. 5, this Figure illustrates an optional use of solar radiation range between 920 nm-1050 nm. For example, a technology of Laser cooling is illustrated with Yb3+ (Ytterbium) doped optical fiber. The adjusted wavelength range (920 nm-1050 nm) is transferred via the fiber optic cable (7) into a tube made of Yb3+ doped optical fiber material on the outside (8), and a transferring material in the inside (9). In the Laser Cooling technology, the material emits photons with higher energy than the energy of the photons it absorbs. As a result of the energy loss, it cools down and experiences temperature decrease. In the particular case of Yb3+ the active wavelength, namely the wavelength range that the material will react in emitting higher energy than absorbing is between 920 nm-1050 nm. In this example the fiber optic cable (7) already carries the right range of spectrum (920 nm-1050 nm) from the system (20) (see FIG. 8), so there is no need for additional filtering.

The same configuration in FIG. 5 for using laser cooling technology applies also to various small ranges, for example, quasi monochromatic ranges. Other non-limiting examples of another ranges and materials are cadmium sulphide with wavelength range of 490 nm-560 nm, Cesium with wavelength of 760 nm-890 nm, 9Be+ with wavelength of around 300 nm and other suitable materials to be found in further research. It should be noted, that the configuration in FIG. 5 is suitable for any type of material for optical fiber with appropriate wavelength range, with difference between emitted and absorbed photon energy sufficient to produce cooling of the fiber and tube surrounding it.

Figure 6:
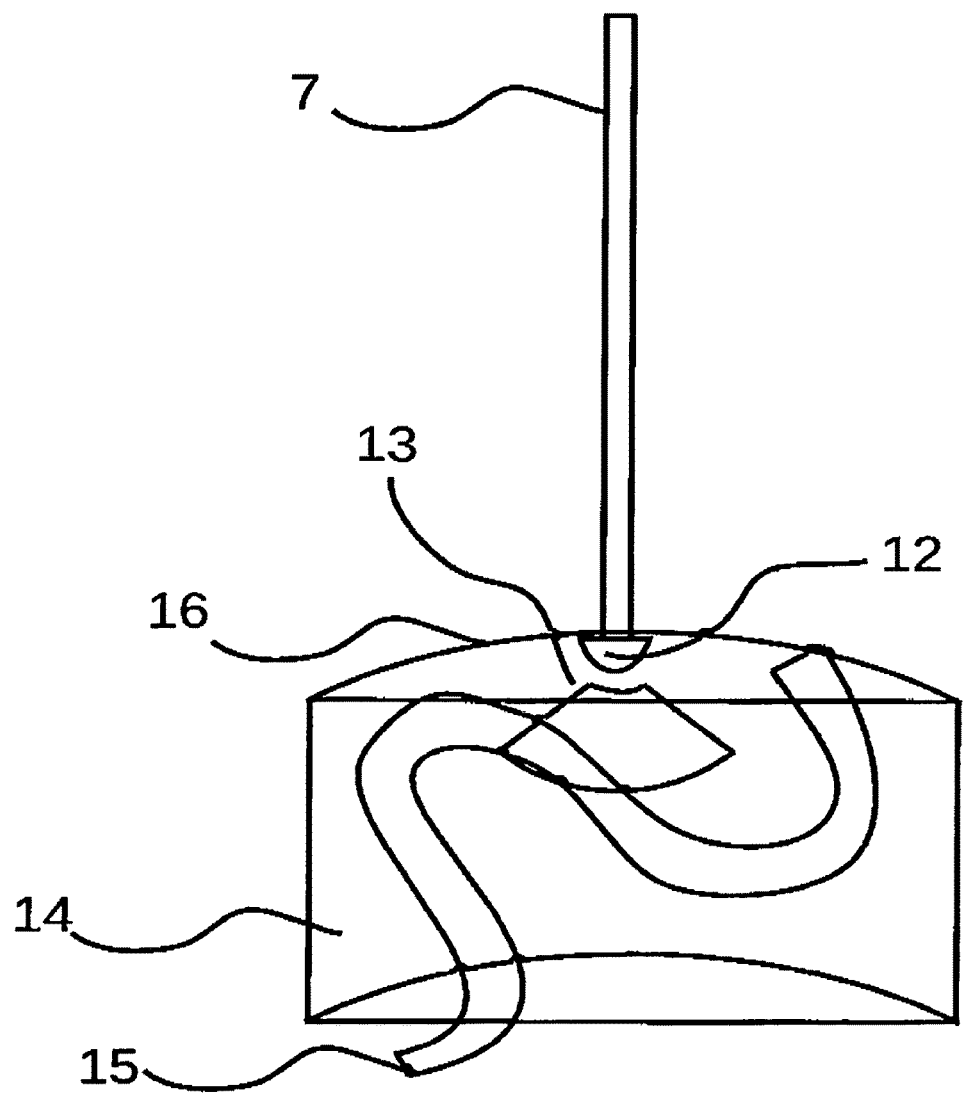
FIG. 6 illustrates yet another optional use of a different range of the spectrum 1050 nm-2500 nm in a method to heat fluids (water for example), or as yet another use of a different range of the spectrum 920 nm-1050 nm as a method to cool the indoors with Laser Cooling technology as projecting on a responsive matter.

Referring to FIG. 6, this Figure illustrates an optional use of solar radiation range between 1050 nm-2500 nm (IR). In the example, the IR radiation (13) transferred through the fiber optic cable (7) is projected by a lens (12) on black body object (14), which is sealed with a seal (16) to vacuum the device and equipped with a water pipe (15) running inside it. The water flowing in the pipe (15) is heated going through the black body device (the same as in solar water heater). In this example the fiber optic cable (7) already carries the right range of spectrum (1050 nm-2500 nm) from the system (20) (see FIG. 8), so there is no need for additional filtering. The lens (12) is a spreading lens intended to spread the IR spectrum (13) to hit the black body (14) evenly.

The same configuration in FIG. 6 for using laser cooling technology applies also to various small ranges (13) transferred through the fiber optic cable (7) is projected by lens (12) on a matching material for the laser cooling technology, for example, quasi monochromatic ranges. Other non-limiting examples of other ranges and materials are cadmium sulphide with wavelength range of 490 nm-560 nm, Cesium with wavelength of 760 nm-890 nm, 9Be+ with wavelength of around 300 nm and other suitable materials to be found in further research.

Figure 7:
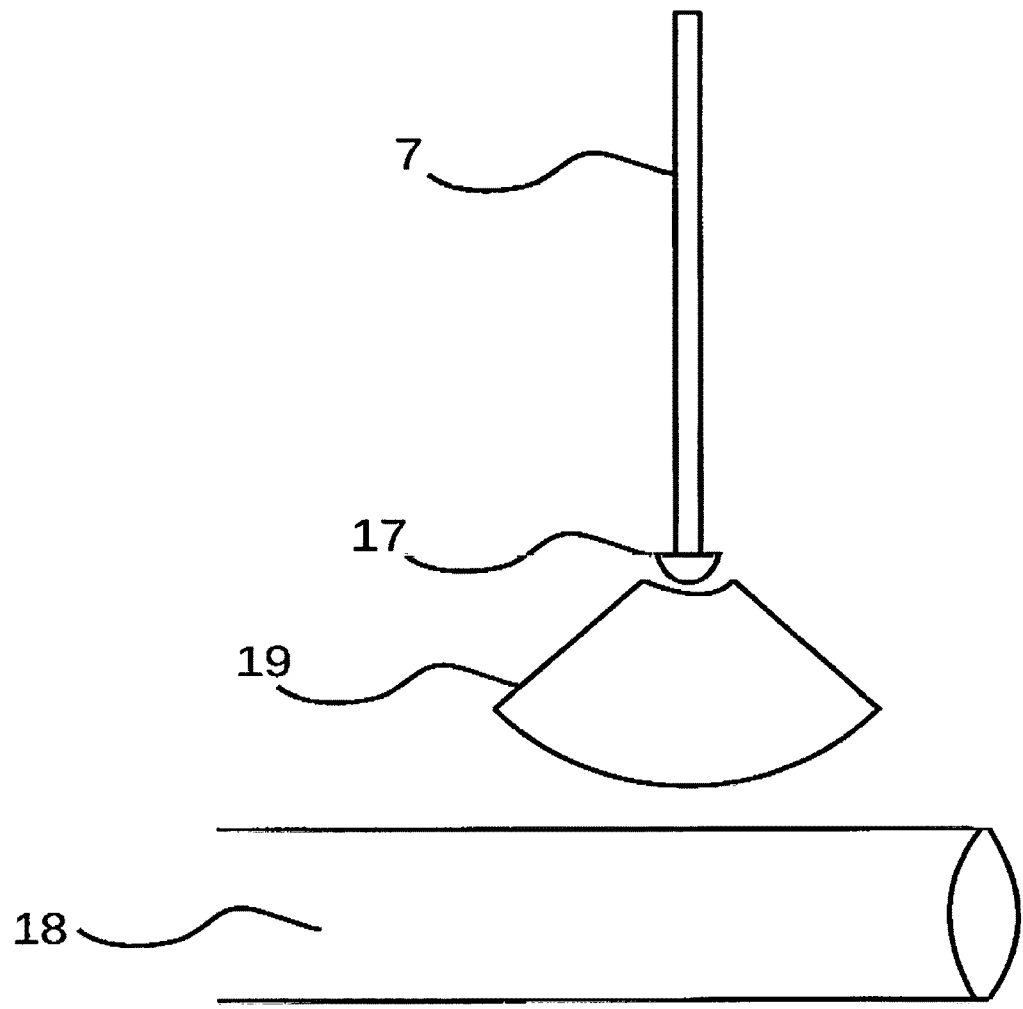
FIG. 7 illustrates yet another optional use of a different range of the spectrum 200 nm-380 nm (the UV range) in its quality of harming biological/living cells as a method to filter water.

Referring to FIG. 7, this Figure illustrates an optional use of solar radiation range between 200 nm-380 nm (UV). Projecting UV radiation continuously on biological cells escalates the deaths rate of these cells. In the example, the UV radiation (19) transferred in the fiber optic cable (7) is projected through a lens (17) on a water pipe (18) to filter the water from living biological organisms, and to clean the water as a result. In this example the fiber optic cable (7) already carries the right range of spectrum (200 nm-380 nm) from the system (20), so there is no need for additional filtering. The lens (17) is a spreading lens intended to spread the UV spectrum (19) to hit the water pipe (18) effectively.

Figure 8:
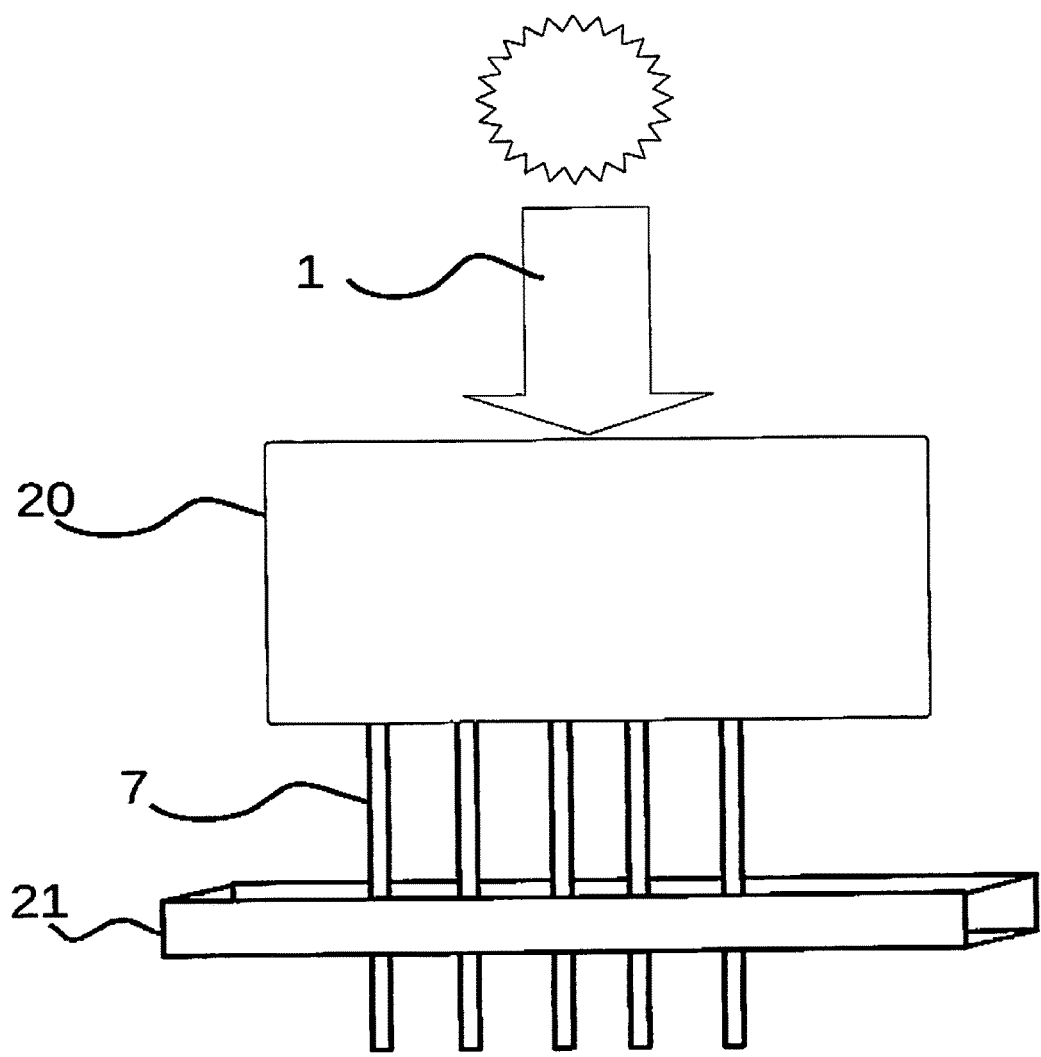
FIG. 8 illustrates an optional installation of the system on the roof of a structure, where part of the system for collecting sunlight is installed on the roof, and fiber optic cables travels from that part through the roof into the indoors.

Referring to FIG. 8, this Figure illustrates an optional installation of the system in a structure. In the Figure, the system (20) is installed on the roof (21) of a structure. This way the solar radiation (1) is collected by the system (20) directly on the roof (21) and is pointed towards the sun. The system then transfers the ranges of radiation through fiber optic cables (7) to the interior of the structure through the roof (21).

Figure 9:
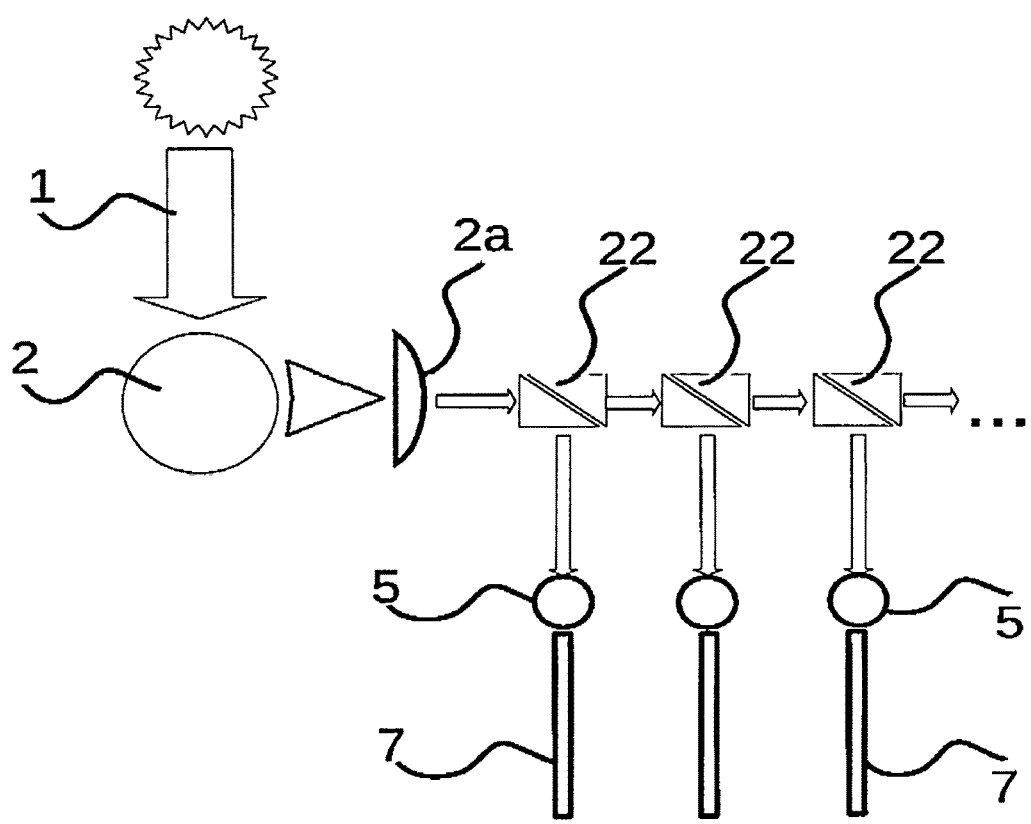
FIG. 9 illustrates the option of splitting the sun radiation by a set of beam splitters where each beam splitter deflect a desired range of spectrum to its appropriate lens/mirror and fiber optic, and transfer the rest of the spectrum to the next beam splitter.

Referring to FIG. 9, this Figure illustrates the system of the present invention where the spectrum is divided by beam splitters (22)—the sun solar radiation (1) being received by the set of concentrating lenses/mirrors (2), (2a). The concentrated radiation hits the radiation splitter which is a set of beam splitters (22). Each beam splitter diverts a different range of the spectrum into its appropriate lens/mirror (5) and transfer the rest of the spectrum to the next beam splitter (22). Different ranges of spectrums are collected and inserted into the fiber optic cables (7) to carry each range to its end product destination.

Although selected embodiments of the present invention have been shown and described, it is to be understood the present invention is not limited to the described embodiments. Instead, it is to be appreciated that changes may be made to these embodiments without departing from the principles and spirit of the invention, the scope of which is defined by the claims and the equivalents thereof.

The invention claimed is:

1. A system for converting electromagnetic radiation from a sun to work, said system comprising:

a set of concentrating lenses or mirrors, each lens or mirror in the set being positioned a selected distance from one another and configured to collect and concentrate the electromagnetic radiation;

a means for splitting the concentrated electromagnetic radiation from the set of concentrating lenses or mirrors into a number of different wavelength ranges, the number of different wavelength ranges equaling a number of second lenses or mirrors and a number of electromagnetically or electrically operated devices, each second lens or mirror having a size and location on a grid that defines which of said different wavelength ranges are collected by each said second lens or mirror, each second lens or mirror configured to collect one of the different wavelength ranges; and at least one fiber optic cable configured to transfer the electromagnetic radiation from each second lens or mirror to one of the number electromagnetically or electrically operated devices, the at least one fiber optic cable being configured to cool itself and being made of or coated with a laser cooling active material selected from the group consisting of Ytterbium with a range of photon emission of 920 nm-1050 nm, semiconductors of elements of the III-V group and semiconductors of elements of the II-VI group, wherein said laser cooling active material is configured to emit photons with higher energy than energy of photons said laser active material absorbs in the system thereby resulting in an energy loss that causes the material to experience a temperature decrease and self-cooling of the at least one fiber optic cable.

2. The system of claim 1, wherein each lens or mirror in the set is made of glass.

3. The system of claim 1, wherein each lens or mirror in the set is made of at least one transparent polymeric material.

4. The system of claim 3, wherein said at least one transparent polymeric material is selected from the group consisting of polystyrene, low density polyethylene, polypropylene and polycarbonate.

5. The system of claim 1, wherein each lens or mirror in the set is parabolic.

6. The system of claim 1, wherein the number of second lenses or mirrors comprises a plurality of second lenses or mirrors, and wherein the electromagnetically or electrically operated devices are configured to operate with the electromagnetic radiation as energy input.

7. The system of claim 1, wherein the laser active cooling material comprises semiconductors of elements of the III-V group selected from the group consisting of gallium arsenide quantum wells, cadmium sulphide having a photon emission range of 760 nm to 890 nm, Cesium having a photon emission range of 760 nm to 890 nm, and 9Be+ Ytterbium having a photon emission range of around 500 nm.

8. The system of claim 1, wherein the laser active cooling material comprises Ytterbium having a photon emission range of 920 nm to 1050 nm.

9. The system of claim 1, wherein the system is located on a roof or outside wall of a closed structure, or outside in close proximity to the closed structure; and
    wherein the at least one fiber optic cable is inserted indoors of the closed structure and connected to the device.

10. The system of claim 1, further comprising a mechanism for detecting and following the sun to allow maximum solar energy input.

11. The system of claim 10, wherein the mechanism is either a single axis tracking system or a two axes tracking system.

12. The system of claim 11, wherein the tracking system is a sensor-enabled detection system comprising solar amplitude sensors or solar position sensors.

13. The system of claim 11, wherein the tracking system is a non-sensory detection system comprising prerecorded solar location, GPS tracking or "dumb" east-west detection.

14. The system of claim 1, wherein the means for splitting comprises a prism, a set of prisms, a diffraction grating, or a set of beam splitters.

15. A unit installation comprising a plurality of systems as claimed in claim 1 configured in an array structure suitable for tracking movement of the sun, each system of the plurality of systems being configured to move synchronically with each other and follow the movement of the sun.

* * * * *